United States Patent [19]
Gatti et al.

[11] Patent Number: 5,731,162
[45] Date of Patent: Mar. 24, 1998

[54] METHOD AND ANALYTICAL DEVICE FOR SIMULTANEOUS IMMUNOASSAY

[75] Inventors: Guido Gatti; Laura Arcioni, both of Monza, Italy

[73] Assignee: Boehringer Mannheim Italia S.p.A., Milan, Italy

[21] Appl. No.: 549,805

[22] PCT Filed: May 27, 1994

[86] PCT No.: PCT/EP94/01723

§ 371 Date: Dec. 6, 1995

§ 102(e) Date: Dec. 6, 1995

[87] PCT Pub. No.: WO94/29729

PCT Pub. Date: Dec. 22, 1994

[30] Foreign Application Priority Data

Jun. 7, 1993 [IT] Italy ............ MI93A1197

[51] Int. Cl.$^6$ .................................. G01N 33/554
[52] U.S. Cl. .................... 435/7.32; 435/7.36; 435/18;
435/23; 435/870; 435/871; 435/961; 435/975;
435/7.94; 436/514; 436/525; 436/528; 436/530;
436/531; 436/541; 436/175; 436/808
[58] Field of Search ................ 435/7.32, 7.36,
435/870, 871, 961, 18, 23, 7.92, 7.94, 975;
436/514, 518, 525, 528, 530, 531, 541,
175, 808

[56] References Cited

U.S. PATENT DOCUMENTS 4,378,344  3/1983  Zahradnik et al. ............ 436/500
4,514,508  4/1985  Hirschfeld .................... 436/518
5,089,389  2/1992  Pelanek et al. ............... 435/7.36
5,415,994  5/1995  Imrich et al. ................. 435/5

FOREIGN PATENT DOCUMENTS 0 444 303 A2  9/1991  European Pat. Off. .

OTHER PUBLICATIONS

International Publication No. WO 87/06620 published Nov. 5, 1987.

Schmitt et al., "Surface Exposed Antigenic Cleavage Fragments of *Neisseria gonorrhoeae* Proteins IA and IB," Infection and Immunity 54(3):841–845 (1986).

Whipple et al., "Isolation and Analysis of Restriction Endonuclease Digestive Patterns of Chromosal DNA from Mycobacterium . . . ," J. of Clin. Micro. 258) 1511–1515 (1987).

Chemical Abstract 101:87322 (1984).

Chemical Abstract 111:219263 (1989).

*Primary Examiner*—Carol A. Spiegel
*Attorney, Agent, or Firm*—Nikaido Marmelstein Murray & Oram LLP

[57] ABSTRACT

The present invention concerns a method and an analytical device for the simultaneous detection of at least two organisms selected from the group consisting of *Chlamydia trachomatis* (CT), *Neisseria gonorrhea* (NG), and Mycoplasma (M) from a single specimen.

18 Claims, 4 Drawing Sheets

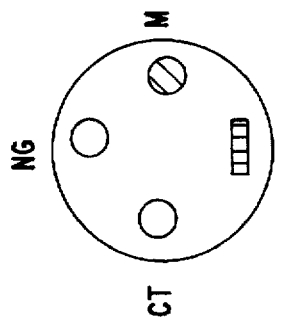
FIG.3C
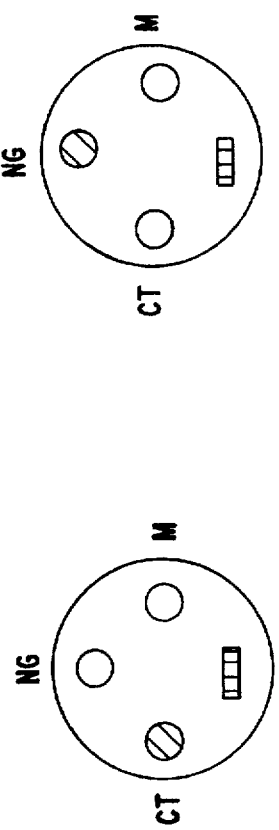
FIG.3B
FIG.3A
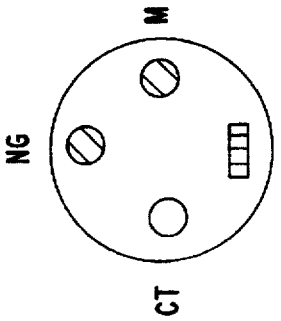
FIG.3G
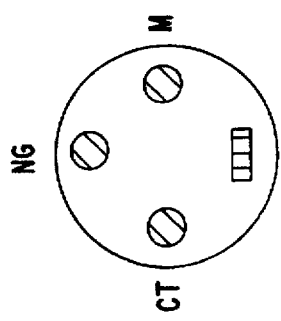
FIG.3F
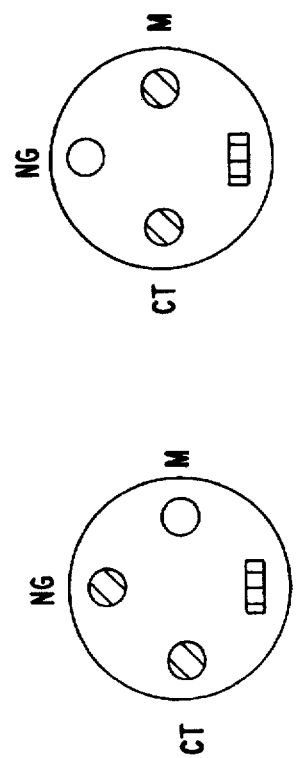
FIG.3E
FIG.3D

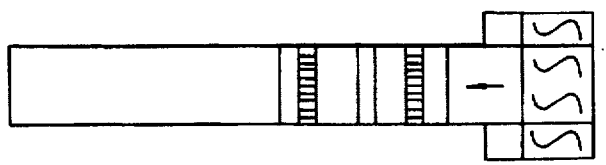
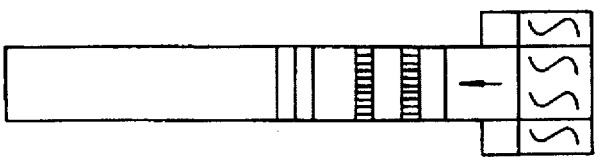
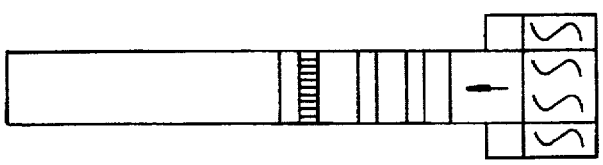
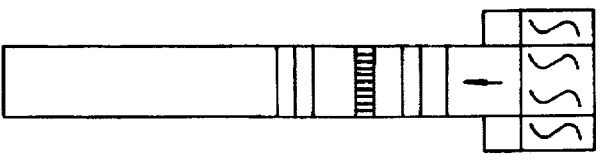
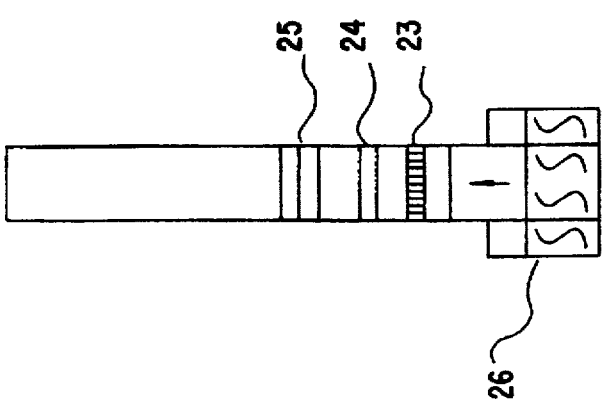

METHOD AND ANALYTICAL DEVICE FOR SIMULTANEOUS IMMUNOASSAY

This application is a rule 371 continuation of PCT/EP94/01723 filed May 27, 1994.

BACKGROUND OF THE INVENTION

The present invention concerns a method and an analytical device for the simultaneous detection of *Chlamydia trachomatis* (CT), *Neisseria gonorrheae* (NG) and Mycoplasma (M) from a single specimen.

The diagnosis of the pathogenic agents responsible of sexually transmitted diseases (STD) such as gonorrhea, urethritis and similar illnesses, currently requires a specimen taken from the infection district as well as a separated analysis for each pathogen, the presence of which has to be verified.

Sampling of the material for the analysis is carried out by swabbing of the vaginal or urethral district.

This application, if repeated, can cause such inconveniences as inflammations or irritations of the mucosae which the swab comes in contact with and is unpleasant for the patient.

As the above mentioned pathogens infect the same organs and can be associated (coinfections), it is clear that the availability of a method and an analytical device which allows the simultaneous detection of CT, NG, M in a single endocervical or urethral specimen would be a welcomed improvement.

This also avoids the discomfort of taking several swabs from the same patient.

PRIOR ART

The European Patent application No. 0 264 036 (Abbott 20.4.88) describes a device and an immunologic method to detect the presence of CT and NG separately.

The European Patent Application No.0444 303 A2 (Becton Dickinson 04.09.91) describes an immunological method to detect *Chlamydia trachomatis* based on a flow-through system involving an extraction step with Proteinase K as extractive agent.

WO 87/06620 (05.11.87) discloses a kit for the contemporaneous detection of different agents responsible of sexually-transmitted diseases, comprising a device having at least one monoclonal antibody selective for each agent to be detected, absorbed on spaced apart reaction zones. The biological sample containing the infectious agent(s) is directly contacted, according to this prior art document, with the device on which the various monoclonal antibodies are immobilized, decreasing thereby the overall diagnostic sensitivity.

In fact, only cell surface antigens would be detectable and it is known that these antigens are liable to easily undergo substantial mutations in response to a variety of conditions, with consequent changes in the binding affinity to the antibodies used for the analysis. Moreover, it is generally accepted as desirable to extract the antigens from the organisms in order to increase assay sensitivity. See, for istance, U.S. Pat. No. 5,089,389.

For these reasons, and in view of the considerable differences existing in the chemical and structural characteristics of the antigens of the organisms responsible of sexually-transmitted disease, the prior-art methods do not allow a sensitive and reliable diagnosis of multiple antigens with only one sampling operation.

SUMMARY OF THE INVENTION

It has now been surprisingly found that antigens from genetically and immunologically different microorganisms such as *Chlamydia trachomatis*, *Neisseria gonorrheae* and Mycoplasma can be simultaneously detected in a biological sample, obtained for instance by scraping or swabbing the genital zone, by subjecting said sample to an incubation step in a suitable reaction media comprising Proteinase K and a lipase, followed by a solid-phase immuno-assay.

The extraction media containing Proteinase K and a lipase effectively releases the antigens of such diverse microorganisms as CT-NG-M from their respective membranes, without modifying their structure thus allowing recognition and binding of these chemically different antigens by their respective antibodies.

The pH of the extraction medium is suitably buffered at values ranging from 7.5 to 9.0.

DETAILED DESCRIPTION OF THE INVENTION

The present invention therefore provides an extraction reagent for extracting antigens of *Chlamydia trachomatis*, *Neisseria gonorrheae* and Mycoplasma from a biological sample comprising Proteinase K, a lipase and buffering agents.

The present invention further provides a method for the simultaneous detection of *Chlamydia trachomatis*, *Neisseria gonorrheae* and Mycoplasma, comprising:

a) incubation of the biological sample in a reaction media comprising Proteinase K and a lipase;

b) incubation, which may follow a specific filtration step, of the reaction mixture in a) with a solution containing three antibody conjugates, each of them specific for one of the antigens specific for one of the three pathogens under examination;

c) contacting of the sample in b) with a solid phase support onto which each of three antibodies specific for the antigens under examination had been immobilized.

In step a) the enzyme(s) are typically suspended in 0.9% NaCl saline solution containing $Ca^{++}$ions and a buffer system so as to mantain the pH values from about 7.5 to about 9, for instance Tris pH 8. The amounts and concentrations of the enzymes are not particularly critical: 0.5 to 10 mcg of the enzyme will be generally sufficient. Incubation will be carried at temperatures from 20° to 50° C., preferably at room temperature, from about 5 to 30 minutes, preferably about 10 minutes.

In step b) monoclonal or polyclonal antibodies conjugated with enzymes, chromophores, coloured particles or heavy metals can be used as reagents.

Monoclonal antibodies conjugated with gold particles, not requiring development steps, are preferred. In case of positivity, the presence of the immunocomplex (Ab conjugated-Ag) is revealed by a red colour in correspondence of the specific immobilized antibody (see FIG. 3).

The conjugation with colloidal gold particles is now a conventional technique and many immunoassays, commercially available, make use of it.

Antibodies directed to the specific antigens of CT, NG, M will be obviously chosen in order to avoid interferences due to cross-reactions. The antibodies in step c) can be directed to the same antigen or epitope.

According to the invention, antibodies anti NG, CT, M, commercially available, can be used after checking, by immunoenzymatic or immunofluorescent assay, the lack of cross-reactions against other pathogens of secondary importance (*Streptococcus pyogenes—Staphylococcus aureus—Escherichia coli*) and bacterial strains normally colonizing the genito-uri-nary tract.

The epitopes recognized by the antibodies have been identified by Western Blot techniques.

The method of the present invention can be conveniently accomplished through a device including a wicking element to suck the liquid, obtained in step b) and a reactive membrane, overlaying the wicking component, on which primary capturing antibodies anti NG, CT, M have been previously immobilized in different well delimited regions.

In accordance to the invention this method can utilize either an immunofiltration or immunochromatography system.

BRIEF DESCRIPTION OF THE DRAWINGS

The invention will now be described with reference to the enclosed drawings wherein:

FIGS. 3A–3G show the reading zones of the device of FIG. 1 in case of positivity for one or more pathogens under analysis;

FIGS. 6A–6E show the reading bands of the strip of FIG. 4 in case of positivity for one or more pathogens under analysis.

Figure 1:
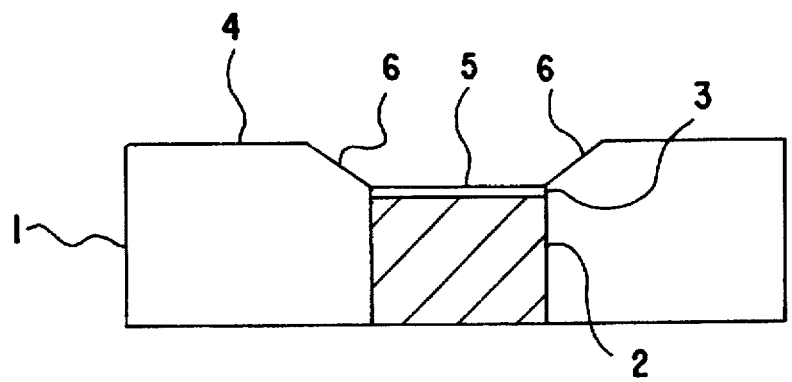
FIG. 1 is a cross section view of the device.

In relation to FIG. 1, the reference number 1 points out a semi-rigid flexible structure (generally in plastic material) carrying a thick filtering layer (2) inside, onto the upper surface of which, a membrane of nitrocellulose (3) or other similar material is located.

The above portion (4) of the this frame shows a round central opening (5) with converging walls, in shape of a funnel (6), exposing the reactive membrane thus delimiting the reading window.

Figure 2:
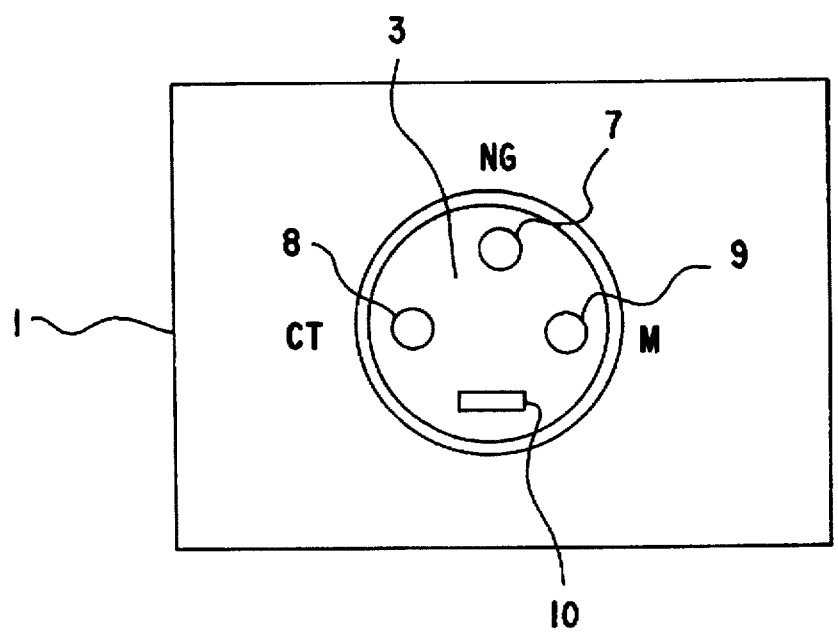
FIG. 2 is a top view of the device of FIG. 1.

In FIG. 2, the reference numbers 7, 8, 9 show the regions in which antibodies anti CT, NG, M have been immobilized.

For ease of use, the initials in this description to designate the pathogens can be reported directly on the device next to the corresponding region.

The reference number 10 points out a built-in-control in which an anti Fc antibody has been immobilized, and which is capable of binding the Fc fragment of all the tracers used in the step b) of the method.

This region, will always give a coloured response if the test has been performed correctly (red when using antibodies conjugated with gold particles).

Figure 4:
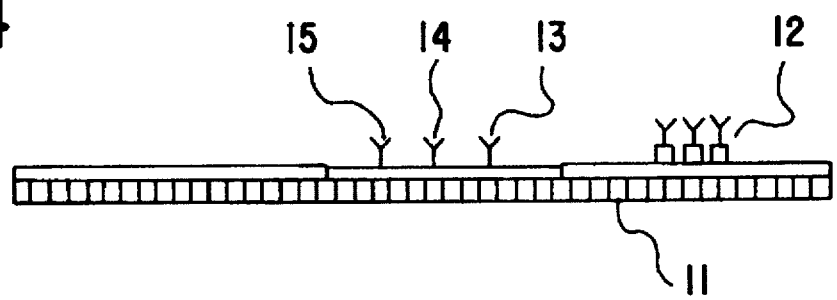
FIG. 4 is a cross section of a strip for immunochromatographic assay.

In relation to FIG. 4, the reference number 11 points out a plastic adhesive support onto which three different solid phases, overlapping at their edges, have been glued. Point 12 shows the gold conjugates and points 13-14-15 represent the three immobilized capturing anti CT-NG-M antibodies.

Figure 5:
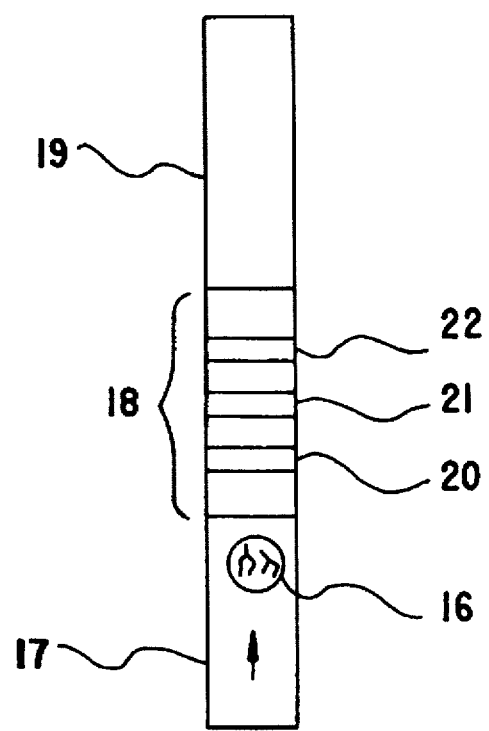
FIG. 5 is a top view of the strip of FIG. 4.

Concerning FIG. 5, the reference number 16 points out the dry reagent constituted of the cocktail of the three conjugates, reversibly adsorbed onto the lower membrane 17. The central reading window 18, is made of reactive nitrocellulose membrane, onto which the primary capturing antibodies anti CT-NG-M have been adsorbed in shape of well limited bands (20-21-22).

The chemical conditions of seeding each antibody as well as the overcoating of the membrane are identical with what reported in the point 1 of example 1.

The upper layer (19) is a common filtering paper, with a very high absorption capacity, to render the flow faster.

Two versions of the same analytical device are possible: vertical and horizontal strip.

In the first case, putting the strip in the sample (previously extracted as reported in the point 2 of example 1) a vertical flow takes place due to capillarity action.

In the second case, the sample is directly poured onto a specific zone of the strip.

If one of the antigens is present in the sample, first it will bind the corresponding conjugate and the immunocomplex then, while migrating, it will be captured onto the relative band.

FIGS. 6A–6E show that in case of positivity for one or more pathogens, one or more red lines (23-24-25), when using gold labelled antibodies, will appear in the reading window. This means that the sandwich Ab-Ag-Ab* has been formed thus revealing an infection or. coinfection state.

FIGS. 6A–6C indicate positivity respectively for CT-NG-M while FIGS. 6D and 6E show two cases of coinfection, even though many other combinations of multiple infections can be found, respectively for CT-NG and CT-M.

In case of negative result, the lines will appear completely colourless.

Obviously, the above configurations are merely exemplifying one of the many variations that can be envisioned by the expert in the art.

The device of the invention will preferably constitute one of the elements of diagnostic kits with the aim to render the execution of the test easier.

A diagnostic kit for the simultaneous detection of CT, NG, M will include, along with a device like the one mentioned above, a mixture of the three conjugated antibodies, one or more enzymatic reagents for the extraction of the antigens from the swab and, if necessary, buffering solutions and other agents or devices suitable to facilitate the execution of the test. The reagents in the kit may be either in liquid or in the so called "dry chemistry" form, i.e. absorbed or immobilized onto suitable carriers.

The following example further illustrate the invention.

EXAMPLE

Immunofiltration system

1) Preparation of the Analytical Device

Loading of the solutions of the monoclonal antibodies anti CT, NG, M and Anti Fc (control).

In correspondence of the reactive zone of the nitrocellulose membrane, the capturing monoclonal antibodies of the title are loaded, with a proper dispenser, in definite and distinct round spots. These antibodies, protein A affinity purified, in phosphate buffer pH=7.2, are, before coating, evaluated to check by immunoenzymatic assay, the lack of cross-reactions against inactivated suspensions of other secondary pathogens as well as strains belonging to the normal flora.

A volume of about 1.5–2 mcl (microliter) at the concentration of 0.8–1.2 mg Ab/ml in borate buffer 0.03M pH 4–5 is spotted for each antibody solution.

As a dispenser, either a capillary or a graduated pipette can be used.

After the radial diffusion of the antibody solution, the membrane is dried in an incubator or under hot-air blow.

Overcoating

Subsequently, the overcoating of the whole surface of the exposed solid phase is carried out by adding a solution of Tris 0.02M with BSA 1%, Sucrose 5%, TWEEN 20 (polyoxyethylene sorbitan monolaurate) 0.3%, Sodium Azide 0.05% pH 8.2 and successive drying as previously described. The overcoating avoid the aspecific cross-reactions.

2) Test Performing

The swab taken from the genital district (vaginal or urethral) is first incubated in an extraction reagent containing physiological saline solution (NaCl 0.9%) $CaCl_2$ 0.005M, Proteinase K (1 mcg/test) prediluted in Tris 0.05M with $CaCl_2$ 0.005M pH 8, and Lipase (10 U/test) in a proper test tube for 10 minutes at room temperature.

The enzymes act by destroying the bacterial membranes getting the specific chemically different antigens free to react with the antibodies.

The suspension is then neutralized by adding a solution of NaCl 1.5% final, condition to optimize the Ab-Ag reaction.

The swab is thus squeezed against the walls of the test-tube; this operation is facilitated because the tube has plastic flexible walls, allowing the release of the liquid soaked into the cotton end of the swab. The swab is disposed of and the sample is ready for the testing step.

At the top of the test tube, containing the extracted sample, is applied a dropper in which a filter (porosity 1 micron) to retain the cellular aggregates that could interfere in the test, is set.

The filtered suspension is incubated with a cocktail solution of the three antibodies anti CT, NG, M conjugated with gold particles for 5 minutes at room temperature.

The three tracers are diluted in Tris 0.02M with BSA 1%, sucrose 5%, TWEEN 20 (polyoxyethylene sorbitan monolaurate) 0.3%, Sodium Azide 0.05% pH 8.2 in a final volume of 0.1–0.2 ml and they all have the same concentration which is measured by reading the optical densities at the wavelenght of 520 nanometers.

At the end of 5 minutes, the solution is directly dropped onto the membrane determining a vertical flow through the membrane.

In presence of the antigen (positivity for one of the three detectable pathogens), the antigen that, in the previous step has been bound by the specific tracer, will be blocked in correspondence of the spot in which the specific primary capturing antibody has been immobilized, giving a red signal.

In absence of the antigen the immunocomplex will not be formed and the conjugate will pass through the membrane leaving the spot completely colorless.

The built-in-control always gives a red colour because the Anti Fc antibody is able to bind the Fc fragment of the three gold conjugates assuring the correctness of the test performing.

3) Reading of the Results

The pink-red colour development in one or more spots indicates positivity for the correspondent pathogenic agent, thus revealing a state of infection or multiple infections (see FIGS. 3A–3F).

The intensity of the colour is proportional to the bacterial charge.

The negative result is visible as colourless white spots.

We claim:

1. A method for simultaneously detecting the presence or absence of at least two microorganisms selected from the group consisting of Chlamydia trachomatis, Neisseria gonorrheae and Mycoplasma, said method comprising:

a) incubating a biological sample in an extraction reagent consisting essentially of proteinase K and a lipase to extract Chlamydia trachomatis antigens, Neisseria gonorrheae antigens and Mycoplasma antigens from said sample thereby producing a reaction mixture;

b) contacting the reaction mixture of step a) with a solution comprising at least two different antibodies conjugated to a detectable label, wherein each said antibody specifically binds to a preselected Chlamydia trachomatis antigen, Neisseria gonorrheae antigen or Mycoplasma antigen extracted in step a), and wherein each said preselected antigen is from a different one of said at least two microorganisms;

c) contacting the reaction mixture of step b) with a solid phase support comprising at least two different, delimited capture areas, wherein each capture area comprises an immobilized antibody which specifically binds to each of said preselected antigens; and, d) detecting the presence or absence of said at least two microorganisms by detecting the presence or absence of each said labelled antibody in each said capture area.

2. The method according to claim 1, further comprising a filtration step prior to step b).

3. The method according to claim 1, wherein said detecting step is carried out by immunofiltration, wherein said solid phase support is a membrane and wherein the absence of said preselected antigens, the reaction mixture of step b) passes through the membrane without binding to said immobilized antibodies.

4. The method according to claim 1, wherein said detecting step is carried out by immunochromatography, wherein said solid phase support is a strip through which said reaction mixture of step b) flows due to capillary action, and wherein in the absence of said preselected antigens, the reaction mixture of step b) flows through the strip without binding to said immobilized antibodies.

5. The method according to claim 4, wherein said strip comprises (I) a membrane comprising said capture areas and (ii) an absorbent wicking component adjacent to said membrane such that said wicking component absorbs the reaction mixture of step b), and wherein said strip is provided in a test device.

6. The method according to claim 5, wherein said wicking component is located at one end of said strip such that the reaction mixture of step b) flows by capillary action from said wicking component through said membrane.

7. The method according to claim 6, wherein said strip is positioned vertically, or horizontally.

8. The method according to claim 1, wherein said detectable label is an enzyme.

9. The method according to claim 1, wherein said detectable label is colloidal gold or a heavy metal label.

10. The method according to claim 1, wherein said detectable label is a chromophore.

11. The method according to claim 1, wherein said solid phase support further comprises a separate, delimited control region comprising an immobilized anti Fc antibody which binds an Fc fragment of said at least two labelled antibodies.

12. The method according to claim 1 for simultaneously detecting two microorganisms selected from the group consisting of Chlamydia trachomatis, Neisseria gonorrheae and Mycoplasma.

13. An extraction reagent for extracting antigens of Chlamydia trachomatis, Neisseria gonorrheae and Mycoplasma from a biological sample, consisting essentially of proteinase K, a lipase and buffering agents.

14. A diagnostic kit for simultaneously detecting the presence or absence of at least two microorganisms selected from the group consisting of *Chlamydia trachomatis, Neisseria gonorrheae* and Mycoplasma, said kit comprising:

a) an extraction reagent consisting essentially of proteinase K and a lipase effective to extract *Chlamydia trachomatis* antigens, *Neisseria gonorrheae* antigens and Mycoplasma antigens;

b) a detection reagent comprising at least two different antibodies conjugated to a detectable label, wherein each said antibody specifically binds to a preselected *Chlamydia trachomatis* antigen, *Neisseria gonorrheae* antigen or Mycoplasma antigen extracted by said extraction reagent a), and wherein each said preselected antigen is from a different one of said at least two microorganisms; and, c) a detection device comprising a solid phase support comprising (i) an immunoreactive membrane comprising at least two different, delimited capture areas, wherein each capture area comprises an immobilized antibody which specifically binds to each of said preselected antigens, and (ii) an adjacent absorbent wicking component, wherein said extraction reagent is in a separate container from said detection device.

15. The kit according to claim 14 wherein said immunoreactive membrane comprises a capture area comprising an immobilized antibody which specifically binds to a preselected antigen for each of said *Chlamydia trachomatis, Neisseria gonorrheae* and Mycoplasma microorgansims.

16. The kit according to claim 14, wherein said detectable label is colloidal gold.

17. The kit according to claim 14, wherein said extraction reagent is in liquid form; said solid phase support is an immunochromatographic test strip; and said detection reagent is either in liquid form or is reversibly adsorbed onto said strip upstream of said capture areas.

18. The kit according to claim 1, wherein said detection reagent is reversibly adsorbed onto said immunoreactive membrane upstream of said capture areas.

* * * * *